United States Patent [19]
Wolf, Jr.

[11] Patent Number: 6,059,968
[45] Date of Patent: May 9, 2000

[54] SYSTEMS FOR PROCESSING AND STORING PLACENTA/UMBILICAL CORD BLOOD

[75] Inventor: Ludwig Wolf, Jr., Inverness, Ill.

[73] Assignee: Baxter International Inc., Deerfield, Ill.

[21] Appl. No.: 09/009,479

[22] Filed: Jan. 20, 1998

[51] Int. Cl.[7] .............................. B01D 36/00; A61M 1/36
[52] U.S. Cl. ........................... 210/252; 210/257.1; 435/2
[58] Field of Search ................................ 210/252, 257.1, 210/513; 435/2; 604/4, 7, 410, 415, 416

[56] References Cited

U.S. PATENT DOCUMENTS

| | | |
|---|---|---|
| Re. 31,135 | 2/1983 | Winchell et al. . |
| 4,004,322 | 1/1977 | Spendlove . |
| 4,004,975 | 1/1977 | Lionetti et al. .......................... 424/534 |
| 4,116,338 | 9/1978 | Weichselbaum . |
| 4,222,379 | 9/1980 | Smith ...................................... 604/410 |
| 4,244,364 | 1/1981 | Grushkin . |
| 4,253,458 | 3/1981 | Bacehowski et al. . |
| 4,294,247 | 10/1981 | Carter et al. ............................. 604/403 |
| 4,479,918 | 10/1984 | Hoeppel .................................. 422/112 |
| 4,505,708 | 3/1985 | Gajewski et al. . |
| 4,630,448 | 12/1986 | Bilstad et al. . |
| 4,714,680 | 12/1987 | Civin . |
| 4,820,297 | 4/1989 | Kaufman et al. . |
| 4,910,147 | 3/1990 | Bacehowski et al. . |
| 4,915,847 | 4/1990 | Dillon et al. . |
| 4,937,194 | 6/1990 | Pattillo et al. ......................... 435/240.2 |
| 4,994,021 | 2/1991 | Smith et al. ................................. 604/6 |
| 5,004,681 | 4/1991 | Boyse et al. ................................ 435/2 |
| 5,053,025 | 10/1991 | Knipscheer . |
| 5,061,620 | 10/1991 | Tsukamoto et al. . |
| 5,100,401 | 3/1992 | Patel ....................................... 604/410 |
| 5,114,672 | 5/1992 | Knippscheer et al. . |
| 5,163,554 | 11/1992 | Lampropoulos . |
| 5,171,234 | 12/1992 | Jepson et al. ............................ 604/411 |
| 5,171,527 | 12/1992 | Knippscheer et al. . |
| 5,188,620 | 2/1993 | Jepson et al. ............................ 604/415 |
| 5,192,553 | 3/1993 | Boyse et al. . |
| 5,306,269 | 4/1994 | Lewis et al. . |
| 5,356,373 | 10/1994 | Dracker . |
| 5,411,499 | 5/1995 | Dudar et al. ............................. 604/411 |
| 5,460,625 | 10/1995 | Johnson .................................. 604/403 |
| 5,622,867 | 4/1997 | Livesey et al. .......................... 436/176 |
| 5,789,147 | 8/1998 | Rubinstein et al. ......................... 435/2 |

FOREIGN PATENT DOCUMENTS

WO96/17514 6/1996 WIPO .

OTHER PUBLICATIONS

Korbling, M. et al., Description of a Closed Plastic Bag System for the Collection and Cryopreservation of Leukapheresis–Derived Blood Mononuclear Leukocytes and CFUc from Human Donors, Transfusion, May/Jun. 1980, PP 293–300, vol. 20, No, 3.

*Primary Examiner*—John Kim
*Attorney, Agent, or Firm*—Daniel D. Ryan; Denise M. Serewicz; Bradford R. L. Price

[57] ABSTRACT

Assemblies and methods process cord blood in a sterile fashion to avoid exposure to bacterial contamination. A transfer tube couples a cord blood processing container to an other container, which, in use, holds a cryopreservative solution. The transfer tube has an interior diameter that is restricted substantially along its entire length, to meter the introduction of cryopreservation solution into cord blood at a desired rate, thereby avoiding damage or trauma to the cord blood cells.

4 Claims, 7 Drawing Sheets

6,059,968

SYSTEMS FOR PROCESSING AND STORING PLACENTA/UMBILICAL CORD BLOOD

FIELD OF THE INVENTION

The invention generally relates to blood collection, processing, and storage systems. In a more specific sense, the invention relates to the collection, processing, and storage of placenta/umbilical cord blood (which in shorthand will simply be called "cord blood").

BACKGROUND OF THE INVENTION

It is known that cord blood contains large numbers of hematopoietic stem and progenitor cells. For this reason, the use of cord blood for therapeutic purposes is indicated, e.g., in the reconstitution of damaged or diseased bone marrow.

The volume of a collected cord blood unit is typically reduced by centrifugation prior to storage and transfusion. Centrifugation separates unneeded mature red blood cells and an equivalent volume of plasma, thereby obtaining a concentration volume of white blood cells, in which the desired stem cells and progenitor cells are found. This concentration of cells is mixed with a suitable cryopreservative solution, e.g., Dimethyl Sulfoxide (DMSO) diluted in a salt solution, for storage at liquid nitrogen temperatures (i.e., −196° C.).

In the past, the processing of cord blood to obtain a therapeutic concentrated of white blood cells suited for storage, has entailed exposing the cord blood and the concentration of desired cells to the atmosphere, usually several times during the course of the procedure. This exposure carries with it the risk of bacterial contamination of the concentrated cell product.

There is a need for systems and methods which allow the processing of cord blood in a sterile "closed" fashion, without significant exposure to the atmosphere.

There is also a need for systems and methods which allow the handling in a sterile closed fashion of cryopreservative solutions at relatively high concentrations, to thereby reduce the overall liquid volume of the processed cord blood.

SUMMARY OF THE INVENTION

The invention provides improved systems and methods for processing cord blood.

One aspect of the invention provides an assembly for processing cord blood comprising a blood processing container and a container for holding a cryopreservative solution. A first tube couples the blood processing container to a source of cord blood. The first tube has a first interior diameter. A second tube couples the blood processing container to the holding container. The second tube has an entire length and a second interior diameter that is less than the first interior diameter substantially along its entire length. The second interior diameter and the entire length of the second tube serve to restrict passage of the cryopreservative solution from the holding container to the blood processing container, to thereby achieve a metered flow rate.

In a preferred embodiment, the holding chamber carries a device adapted and arranged to affect a sterile connection with a source of cryopreservative solution. In this embodiment, the second tube integrally connects the holding container to the blood processing container.

This aspect of the invention permits the introduction of concentrated cryopreservative solutions into cord blood in a closed sterile fashion, and at a metered flow rate that avoids causing damage or trauma to the stem cells or progenitor cells.

Another aspect of the invention provides an assembly for processing cord blood comprising a blood processing container and a container for holding a cryopreservative solution. A first tube couples the blood processing container to a source of cord blood. A second tube couples the blood processing container to the holding container. The blood processing container is made of a first material that degrades as a result of exposure to high concentrations of cryopreservative solution. The holding container is made of a different, second material, which is more compatible with the cryopreservative solution and which does not degrade as a result of exposure to the solution at the high concentrations.

This aspect of the invention permits the handling of concentrated cryopreservative solutions into cord blood in a closed sterile fashion.

Other features and advantages of the invention will be pointed out in, or will be apparent from, the drawings, specification and claims that follow.

Figure 1:
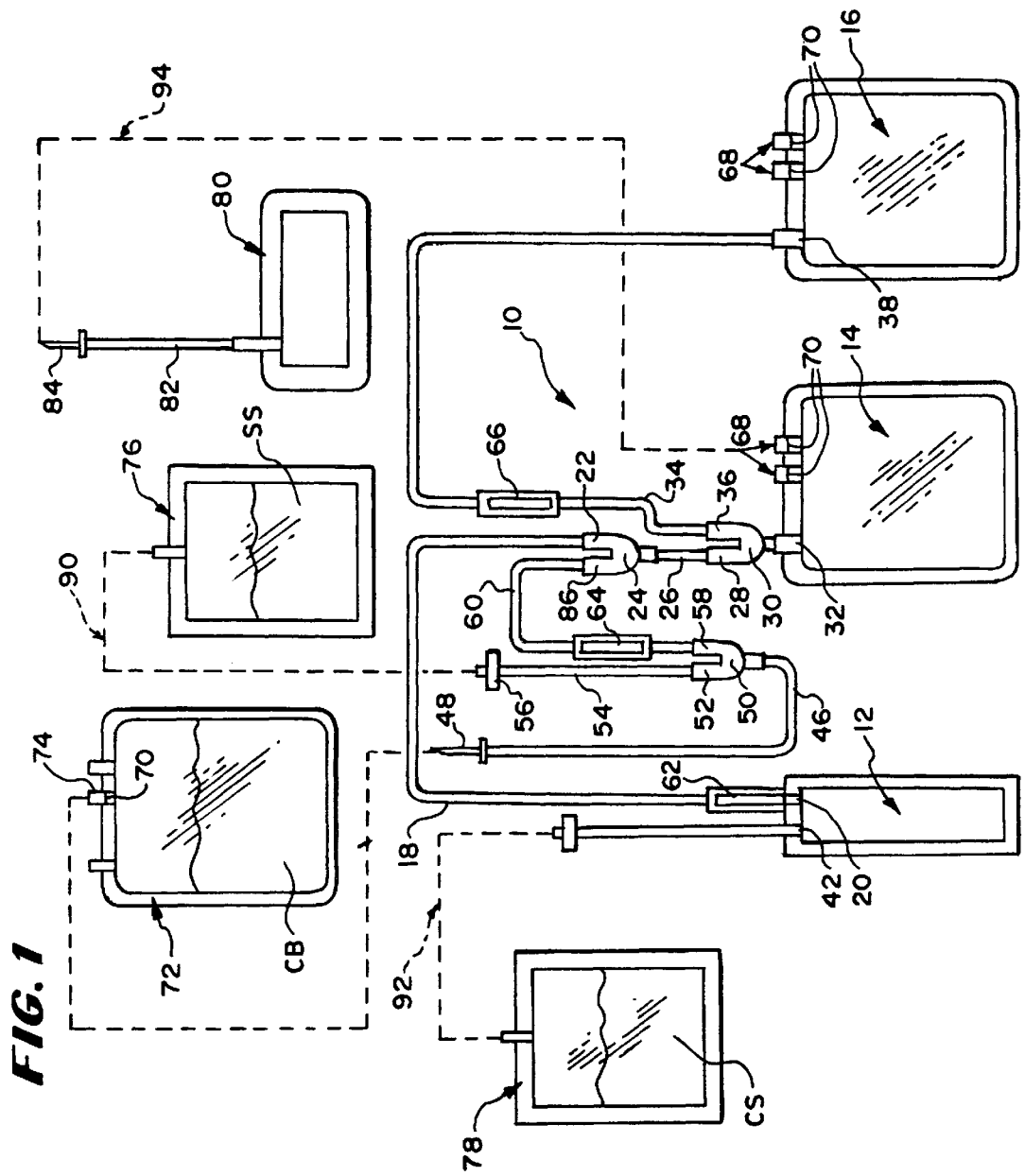
FIG. 1 is a schematic view of a cord blood processing and storage assembly 10, which embodies features of the invention.

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

FIG. 1 shows a cord blood processing and storage assembly 10.

The assembly 10 includes a first, second, and third containers 12, 14, and 16, which are interconnected by seven flexible transfer tubes 18, 26, 34, 40, 46, 54, and 60.

The first transfer tube 18 is, at one end, integrally connected to a port 20 of the first container 12, which, in use, serves as a holding container for cryopreservative solutions prepared at relatively high concentrations. The opposite end of the first transfer tube 18 is integrally connected to one leg 22 of a Y-connector 24, which is, in turn, integrally connected to one end of the second transfer tube 26.

The opposite end of the second transfer tube 26 is integrally connected to one leg 28 of a Y-connector 30, which is itself integrally attached to a port 32 of the second container 14, which, in use, serves as a blood processing container. The third transfer tube 34 is, at one end, integrally attached to an other leg 36 of the Y-connector 30 and, at its opposite end, integrally connected to a port 38 of the third container 16, which, in use, serves as a liquid transfer container.

The fourth transfer tube 40 is integrally coupled to a second port 42 of the first container 12. The fourth transfer tube 40 carries an integrally attached in-line filter 44. The filter 44 includes a conventional microporous membrane material that allows liquid and air to pass, but otherwise prevents the ingress of bacteria. The material is available, e.g., from Gelman Filters, under the trade name VERSAPOR 200, which has a 0.2 μm pore size.

The fifth transfer tube 46 carries, at one end, a conventional blood spike 48 and, at its opposite end, is integrally coupled to a Y-connector 50. One leg 52 of the Y-connector 50 is integrally connected to the sixth transfer tube 54. The sixth transfer tube 54 carries an integrally attached inline filter 56. Like the in-line filter 44, the filter 56 includes a conventional microporous membrane material that allows liquid and air to pass, but otherwise prevents the ingress of bacteria.

An other leg 58 of the Y-connector 50 is integrally connected to the seventh transfer tube 60. The opposite end of the seventh transfer tube 60 is integrally connected to an other leg 86 of the Y-connector 24, which leads to the port 32 of the second container 14 via the second transfer tube 26 and Yconnector 30, already described.

In the illustrated embodiment, the transfer tubes 18, 26, 34, 40, 46, 54, and 60 are made from medical grade plasticized polyvinyl chloride plastic. However, other flexible medical grade plastic materials can be used.

Conventional in-line frangible cannulas 62, 64, and 66 are located in the first, third, and seventh transfer tubes 18, 34, and 60, respectively. Each cannula 62, 64, and 66 normally closes its respective tube to fluid flow. Each cannula 62, 64, and 66 can be constructed in various ways. U.S. Pat. Nos. 4,181,140 and 4,294,247 disclose representative constructions for the cannula, which are incorporated herein by reference. Alternatively, an external roller clamp or C-clamp of conventional construction could be used for the same purpose.

In the illustrated embodiment, the second and third containers 14 and 16 comprise conventional blood bags made of from medical grade plasticized polyvinyl chloride plastic. However, other flexible medical grade plastic materials can be used.

In the illustrated embodiment, the second and third containers 14 and 16 each include one or more administration ports 68, which are normally sealed by pierceable membranes 70. For reasons that will be discussed later, the first container 12 is not made from polyvinyl chloride plastic material.

Figure 2:
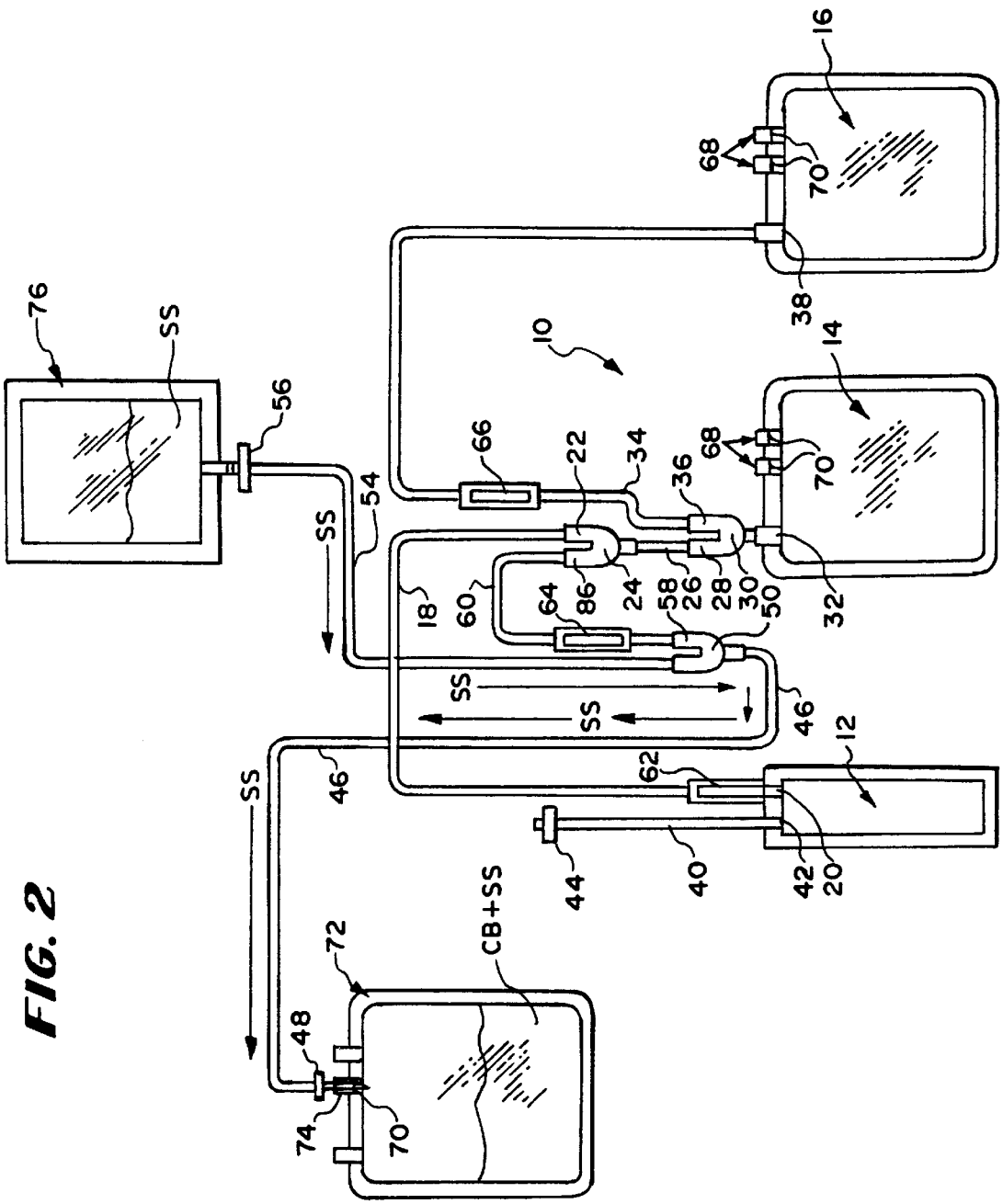
FIG. 2 is a schematic view of the assembly shown in FIG. 1, in use to transfer a sedimentation enhancing solution to a blood collection bag containing cord blood.

In use, a unit of cord blood CB has been previously collected in a conventional flexible blood collection bag 72, which also contains a conventional anticoagulant solution. The blood collection bag 72 is equipped with an outlet port 74, which is normally closed by a membrane 70. As FIG. 2 shows, the spike 48 carried at the end of the fifth transfer tube 46 is inserted into the outlet port 74 to pierce and open the membrane 70 (as is also indicated by dotted line 88 in FIG. 1).

To enhance centrifugal separation of mature red blood cells, a sedimentation enhancing solution SS, e.g., a 6% concentration of hydroxy ethyl starch, is conveyed into the blood collection bag 72 for mixing with the anticoagulated cord blood CB. As FIG. 2 shows, a reagent container 76 holding the solution SS is coupled to the in-line filter 56 carried at the end of the sixth transfer tube 54 (as is also indicated by dotted line 90 in FIG. 1). The reagent container 76 is supported above the blood collection bag 72, so the solution SS flows by gravity through the filter 56 and the fifth and sixth transfer tubes 46 and 54 into the blood collection bag 72, where it mixes with the anticoagulated cord blood CB. The solution SS causes mature red blood cells to aggregate into loose clumps in the blood collection bag 72, a process known as "rouleauing."

Figure 3:
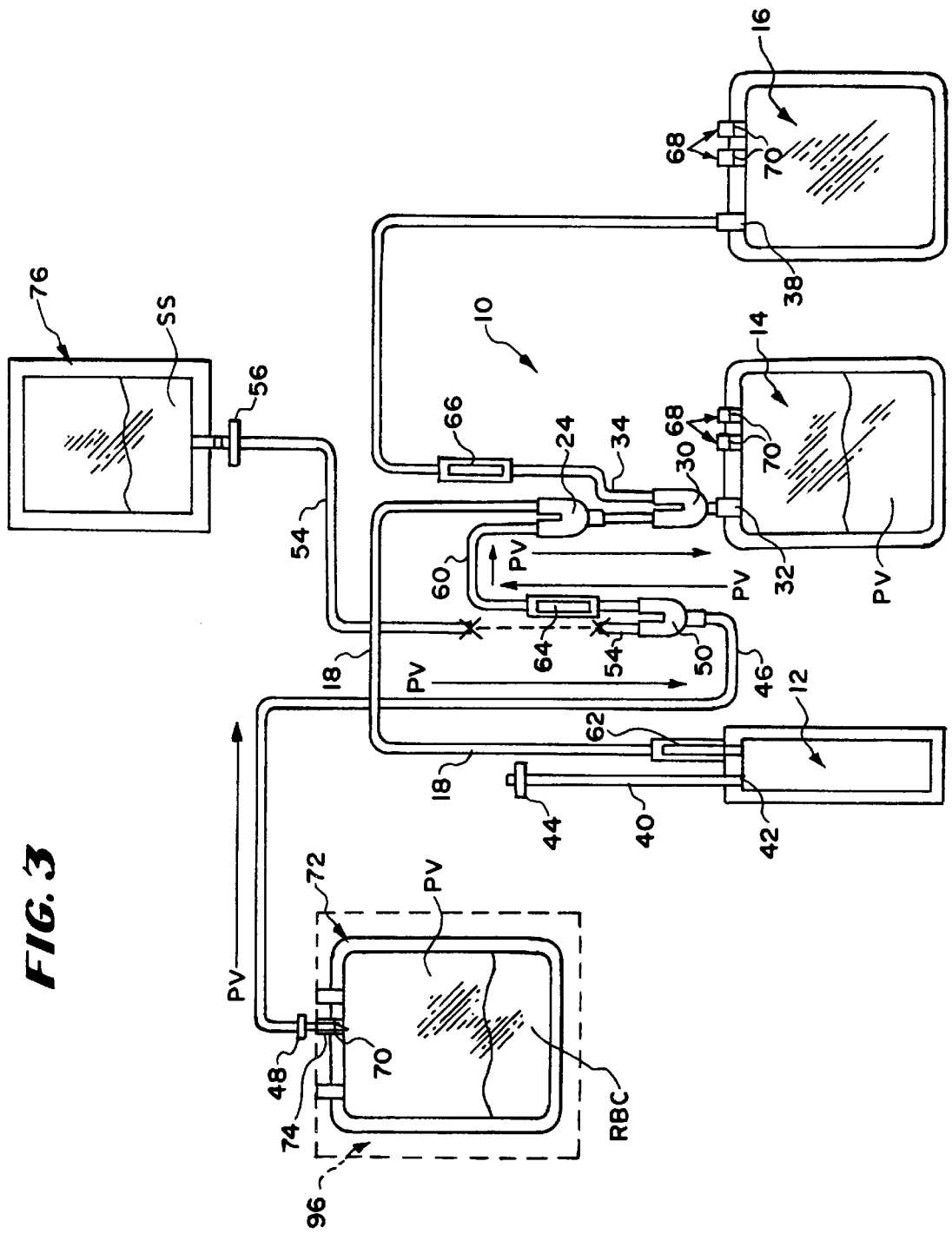
FIG. 3 is a schematic view of the assembly shown in FIG. 1, in use to transfer a residual volume of plasma, which contains desired stem and progenitor cells, into one container of the system, following centrifugation in the blood collection bag, which retains the centrifugally separated mature red blood cells.

As FIG. 3 shows, the empty blood reagent container 76 can be separated from the assembly 10 by heat sealing the sixth transfer tube 54. The detachment can be accomplished using, e.g., a conventional heat sealing device (for example, the Hematron® dielectric sealer sold by Baxter Healthcare Corporation), which forms a hermetic, snap-apart seal in the tube 54 (this type of seal is schematically shown by an "x" throughout the Figures).

The blood collection bag 72 and the remaining parts of the assembly 10 attached to it are placed into a blood centrifuge. The blood collection bag 72 is oriented in the centrifuge so that its bottom faces away from the rotational axis during centrifugation. The centrifuge gently spins the blood collection bag 72 at a low rate of rotation, e.g., five minutes at 50 gs. The mature red blood cells RBC separate toward the high-G portion of the centrifugal field (at the bottom of the blood collection bag 72), while a residual plasma volume PV, which carries the white blood cells, the desired stem cells, and progenitor cells, occupies the low-G portion of the field (at the top of the blood collection bag 72).

As FIG. 3 shows, following centrifugation, the blood collection bag 72 and attached assembly 10 are removed from the centrifuge. The blood collection bag 72 (holding the separated components RBC and PV) is placed in a conventional V-shaped plasma press 96 or the like, with the top of the bag 72 facing upwards. The cannula 64 in the seventh transfer tube 60 is broken open. The press 96 squeezes the blood collection bag 72 to convey the residual plasma volume PV (and its therapeutic contents) into the second container 14. The squeezing process is visually monitored manually, or automatically by optical sensing, to keep the separated red blood cells RBC in the blood collection bag 72.

Figure 4:
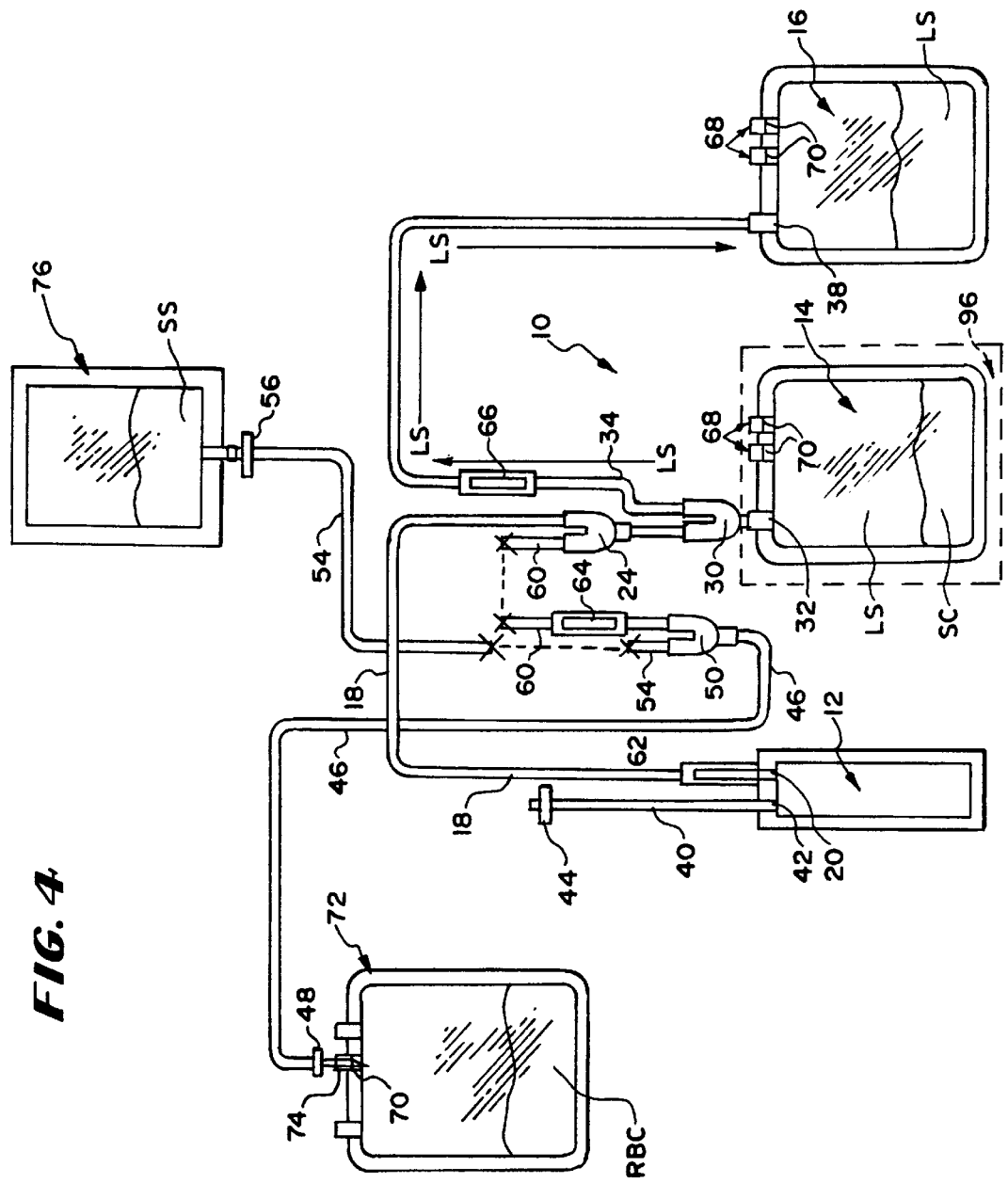
FIG. 4 is a schematic view of the assembly shown in FIG. 1, in use to transfer a liquid supernatant into an other container of the system, following centrifugation to separate a concentration of desired stem and progenitor cells, which one container in the system retains for further processing.

As FIG. 4 shows, the blood collection bag 72 and most of the seventh transfer tube 60 can now be separated from the assembly 10, by forming a hermetic, snap-apart seal ("x") in the seventh transfer tube 60 between the Y-connector 24 and the cannula 64. The second container 14 and the remaining parts of the assembly 10 are placed back into the centrifuge, with the bottom of the second container 14 oriented in the centrifuge to face away from the rotational axis. The centrifuge spins the second container 14 at a higher rate of rotation and for a longer time than before, e.g., ten minutes at 400 gs. The white blood cells and the desired stem progenitor cells SC, separate toward the high-G portion of the centrifugal field (at the bottom of the second container 14), while the liquid supernatant LS occupies the low-G portion of the field (at the top of the second container 14). The liquid supernatant LS contains most of the plasma, anticoagulant and sedimentation enhancing solution, but is essentially free of blood cells SC.

As FIG. 4 shows, following the second centrifugation step, the second container 14 and attached assembly 10 are removed from the centrifuge. The second container 14 (holding the separated components SC and LS) is placed in the conventional V-shaped plasma press 96 or the like, with the top of the container 14 facing upwards. The cannula 66 in the third transfer tube 34 is broken open. The press 96 squeezes the second container 14 to convey the liquid supernatant LS into the third container 16. The squeezing process is manually monitored visually, or automatically by optical sensing, to retain the concentrated mass of white blood cells and desired stem and progenitor cells SC in the second container 14.

Figure 5:
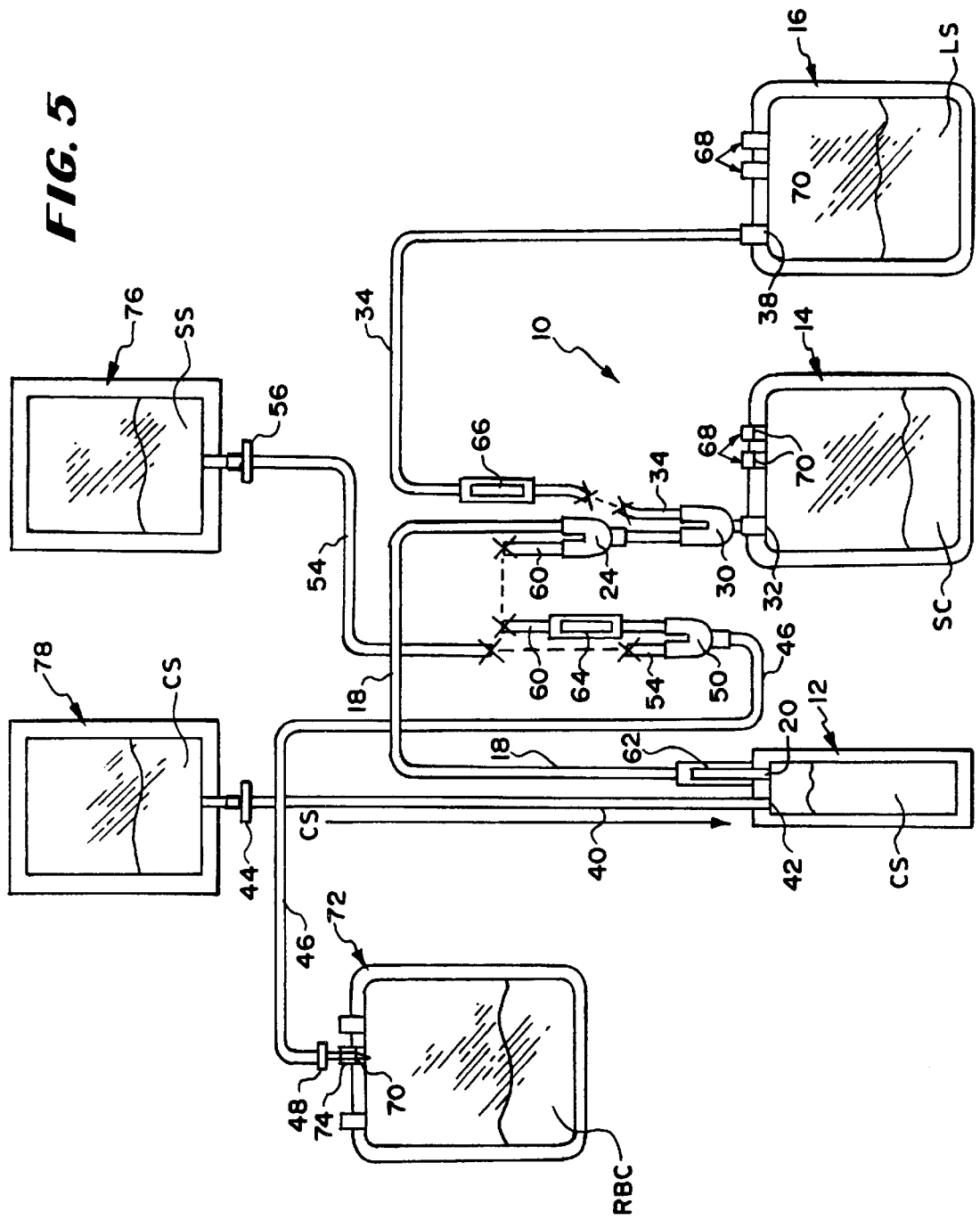
FIG. 5 is a schematic view of the assembly shown in FIG. 1, in use to transfer a concentrated cryopreservative solution into a special holding container in the system.

As FIG. 5 shows, the third container 16 is separated from the assembly 10 by forming a hermetic, snap-apart seal ("x") in the third transfer tube 34 between the Y-connector 30 and the cannula 66. At this stage of the process, as FIG. 5 shows, the first container 12, the second container 14, and the first, second, and fourth transfer tubes 18, 26, and 40 remain integrally connected.

As FIG. 5 further shows, a reagent container 78 of selected cryopreservative solution CS, e.g., DMSO, is coupled to the in-line filter 44 carried at the end of the fourth transfer tube 40 (as is also indicated by dotted line 92 in FIG. 1). The reagent container 78 is held above the first container 12, so that the cryopreservative solution CS drains into the first container 12. When the first container 12 holds a sufficient volume of cryopreservative solution CS, the reagent container 78 is separated from the assembly 10, by forming a hermetic, snap-apart seal ("x") in the fourth transfer tubing 40 (as FIG. 6 shows).

To minimize fluid processing and storage volumes, the cryopreservative solution CS is preferable concentrated, using, e.g., a 50% DMSO solution. However, it has been discovered that a concentrated DMSO solution will slowly degrade and dissolve conventional medical grade polyvinyl chloride plastic material. Therefore, the first container 12 should not be made from this material. Instead, the first container 12 is made from polyurethane, polyolefin, blends of polyolefin and KRATON™ thermoplastic elastomer (Shell Chemical) or nylon, and fluropolymers, which are not degraded or dissolved by contact with a concentrated DMSO solution.

Figure 6:
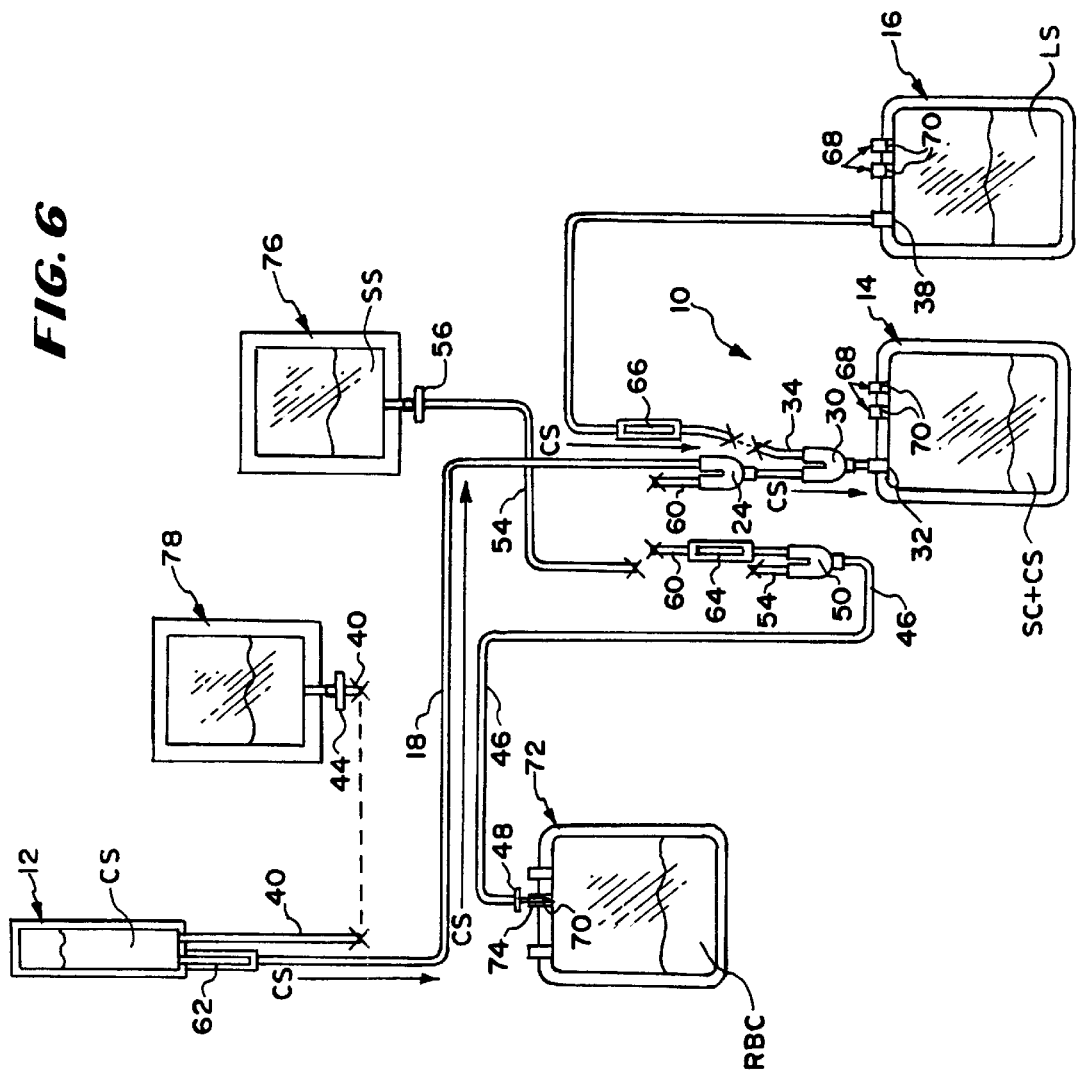
FIG. 6 is a schematic view of the assembly shown in FIG. 1, in use to meter concentrated cryopreservative solution from the special holding container in the system into the container in the system which retains the concentration of desired stem and progenitor cells.

As FIG. 6 shows, the first container 12 containing the cryopreservative solution CS is supported above the second container 14, and the cannula 62 is broken. The cryopreservative solution CS flows by gravity through the first and second transfer tubes 18 and 26 into the second container 14, where it mixes with the concentrated mass of white blood cells and desired stem and progenitor cells SC.

When using a concentrated cryopreservation solution CS, the rate at which the solution CS is introduced into the cell concentration SC in the second container 14 must be metered, to avoid damage to the cell concentration SC. Accordingly, in the illustrated embodiment, the diameter and length of the first transfer tube 18 are selected to obtain a desired metered flow rate. For example, when a 50% DMSO solution is used, the first transfer tube 18 is made smaller in diameter than the other transfer tubes, having, e.g., a restricted interior diameter of about 0.015 inch over a length of nine inches. This combination of restricted interior diameter over a selected length will slowly meter about 5 ml of concentrated solution into the second container 14 over a time span of about twenty (20) minutes.

Figure 7:
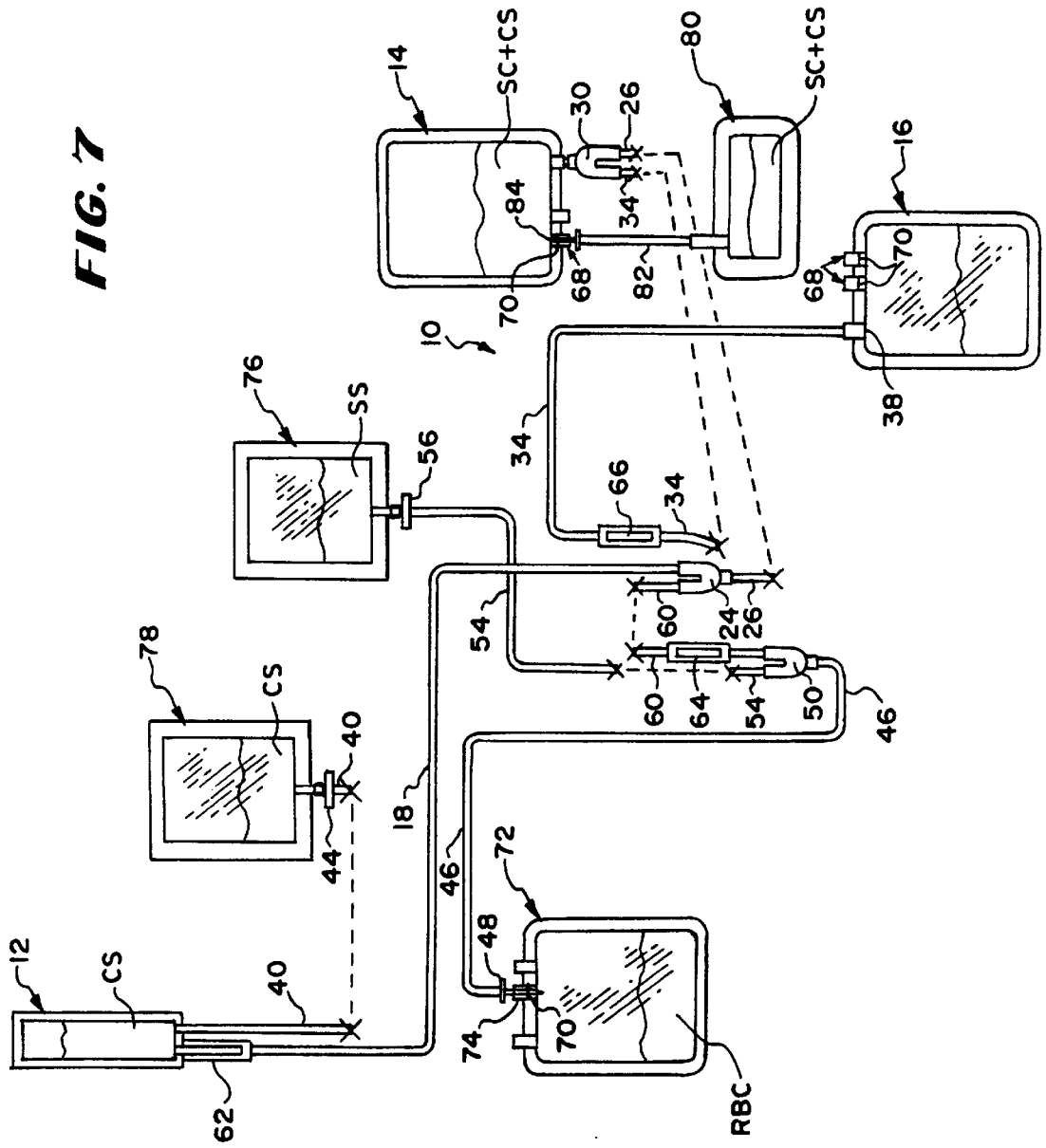
FIG. 7 is a schematic view of the assembly shown in FIG. 1, in use to transfer desired stem and progenitor cells, mixed with concentrated cryopreservative solution, into a freezing bag for storage.

As FIG. 7 shows, after metering in the desired volume of cryopreservative solution CS, the first container 12 and first transfer tube 18 are separated from the assembly 10 by forming a hermetic, snap-apart seal ("x") in the second transfer tube 26 between the two Y-connectors 24 and 30. This leaves the second container 14, holding the concentrated cell mass SC mixed with cryopreservative solution CS.

As FIG. 7 shows, the contents SC/CS of the second container 16 can now be transferred to a suitable freezing container 80 for storage. The freezing container 80 includes an integrally attached transfer tube 82, which carries a conventional blood spike 84. The blood spike 84 pierces and opens the membrane 70 in a selected administration port 68 on the second container 14, allowing the transfer of the cell mass SC and cryopreservation solution CS into the freezing container 80 (as is also indicated by dotted line 94 in FIG. 1). Following the transfer, the transfer tube 82 can be heat sealed to separate the freezing container 80 from the second container 14.

In the illustrated embodiment, the freezing container 80 comprises first and second sheets of flexible plastic material capable of withstanding cryogenic temperatures, like polyethylene, polypropylene, ethylene-vinyl-acetate, fluropolymers, or copolymers of these materials. During manufacture, the sheets have been softened by heat and exposed to interior positive pressure to assume a preformed, stress-relieved geometry, which is resistant to material fatigue and failure. Further details of the construction and manufacture of the freezing container are found in copending, commonly assigned patent application Ser. No. 08/982,758, filed Dec. 2, 1997, and entitled "Heat and Pressure Formed Flexible Containers and Methods for Making Them."

As shown in FIG. 1, the assembly 10 comprises an integral system of fluid-free or "dry" containers. This arrangement simplifies sterilization and serves to mediate the application of the regulatory requirements governing integral, fluid-containing assemblies. It should be appreciated, however, that the assembly 10 can include one or more integrally attached fluid containers. For example, the container 76 holding the sedimentation enriching solution SS can be integrally attached to the sixth transfer tube 54, thereby making the use of the in-line filter 56 unnecessary. Alternatively, the container 76 holding the sedimentation enriching solution SS can be integrally attached or otherwise sterile coupled to the blood collection bag 72 itself, thereby making both the sixth transfer tube 54 and the in-line filter 56 unnecessary. Alternatively, or in combination, the container 78 holding the cryopreservative solution CS can be integrally connected to the fourth transfer tube 40, thereby making the use of the in-line filter 44 unnecessary.

Furthermore, conventional sterile connection devices can be used instead of the in-line filters 44 or 56 or the spikes 48 or 84. Such sterile connection devices are described in Granzow et al U.S. Pat. Nos. 4,157,723 and 4,265,280, which are incorporated herein by reference. Alternately, a sterile connecting assembly like that disclosed in Spencer U.S. Pat. No. 4,412,835 can be used. Other conventional sterile or aseptic methods can be used as well.

The assembly 10 permits cord blood to be conveniently processed in an environment that remains sterile and "closed" throughout the process. The assembly 10 reduces the work involved in the process and decreases the likelihood of bacterial contamination.

Features and advantages of the invention are set forth in the following claims.

We claim:

1. An assembly for processing cord blood comprising a blood processing container, a holding container for holding a cryopreservative solution, a first tube coupling the blood processing container to a source of cord blood, the first tube having a first interior diameter, and a second tube coupling the blood processing container to the holding container, the second tube having an entire length and a second interior diameter less than the first interior diameter substantially along the entire length, the second interior diameter and the entire length restricting passage of the cryopreservative solution during gravity flow from the holding container to the blood processing container to achieve a metered flow rate without external metering instrumentality.

2. An assembly according to claim 1 wherein the holding container carries a device adapted and arranged to affect a sterile connection with a source of cryopreservative solution.

3. An assembly according to claim 1 wherein the second tube is integrally connected to the blood processing container and the holding container.

4. An assembly for processing cord blood according to claim 1 wherein the blood processing container is made of a first material, and wherein the holding container is made of a second material compatible with the cryopreservative solution and different than the first material.

* * * * *